United States Patent
Patch (10) Patent No.: US 6,754,299 B2
(45) Date of Patent: Jun. 22, 2004

(54) METHODS AND APPARATUS FOR WEIGHTING OF COMPUTED TOMOGRAPHY DATA

(75) Inventor: Sarah K. Patch, Milwaukee, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/211,206

(22) Filed: Aug. 2, 2002

(65) Prior Publication Data

US 2004/0022365 A1 Feb. 5, 2004

(51) Int. Cl.[7] ............................................. A61B 6/03
(52) U.S. Cl. ............................ 378/15; 378/8; 378/901
(58) Field of Search .......................... 378/4, 8, 15, 901

(56) References Cited

U.S. PATENT DOCUMENTS

| | | | |
|---|---|---|---|
| 5,802,134 A | 9/1998 | Larson et al. | |
| 5,881,122 A | 3/1999 | Crawford et al. | |
| 5,887,047 A | 3/1999 | Bailey et al. | |
| 5,889,833 A | 3/1999 | Silver | |
| 5,909,477 A | 6/1999 | Crawford et al. | |
| 6,292,526 B1 | 9/2001 | Patch | |
| 6,324,241 B1 | 11/2001 | Besson | |
| 6,341,154 B1 | 1/2002 | Besson | |
| 6,343,108 B1 * | 1/2002 | Heuscher | 378/4 |
| 6,408,042 B1 * | 6/2002 | Hsieh | 378/4 |
| 6,411,670 B1 | 6/2002 | Besson | |
| 6,415,013 B1 | 7/2002 | Hsieh et al. | |
| 6,421,411 B1 | 7/2002 | Hsieh | |
| 6,459,754 B1 | 10/2002 | Besson et al. | |
| 2002/0122529 A1 * | 9/2002 | Heuscher | 378/4 |

* cited by examiner

*Primary Examiner*—David V. Bruce
(74) *Attorney, Agent, or Firm*—Carl B. Horton, Esq.; Armstrong Teasdale LLP (57) ABSTRACT

A method for reconstructing an image of an object utilizing a computed tomographic (CT) imaging system is provided. The CT system includes a radiation source and a multislice detector array on a rotating gantry, with the radiation source configured to project a beam of radiation through an object and towards. the multislice detector array. The multislice detector array is configured to sense attenuation of the radiation passing through the object. The method for reconstructing an image includes helically scanning an object with a computed tomographic imaging system to acquire a plurality of views of projection data at a plurality of gantry angles and a plurality of cone angles, generating a plurality of cone angle dependent weights that are inversely correlated to an absolute value of a cone angle, and weighting the projection data using the cone angle dependent weights.

19 Claims, 4 Drawing Sheets

60

62 — Helically scanning an object with a computed tomographic imaging system to acquire a plurality of views of projection data at a plurality of gantry angles and a plurality of cone angles.

64 — Generating a plurality of cone angle dependent weights that are inversely correlated to an absolute value of a cone angle.

66 — Weighting the projection data using the cone angle dependent weights.

METHODS AND APPARATUS FOR WEIGHTING OF COMPUTED TOMOGRAPHY DATA

BACKGROUND OF THE INVENTION

This invention relates generally to methods and apparatus for computed tomographic (CT) image reconstruction, and more particularly to weighting of data collected in a CT system.

At least one known computed tomography (CT) imaging system uses an in creased table speed to reduce scan time. An increased table speed reduces the quantity of data samples acquired along a plurality of helical trajectories within an image reconstruction space. A reduction in the quantity of data samples combined with a plurality of cone beam effects may produce an image with decreased image quality.

BRIEF DESCRIPTION OF THE INVENTION

In one aspect, a method for reconstructing an image of an object utilizing a computed tomographic (CT) imaging system is provided. The CT system includes a radiation source and a multislice detector array on a rotating gantry, with the radiation source configured to project a beam of radiation through an object and towards the multislice detector array. The multislice detector array is configured to sense attenuation of the radiation passing through the object. The method for reconstructing an image includes helically scanning an object with a computed tomographic imaging system to acquire a plurality of views of projection data at a plurality of gantry angles and a plurality of cone angles, generating a plurality of cone angle dependent weights that are inversely correlated to an absolute value of a cone angle, and weighting the projection data using the cone angle dependent weights.

In another aspect, a computed tomographic (CT) imaging system for reconstructing an image of an object is provided. The computed tomographic (CT) imaging system includes a radiation source and a multislice detector array on a rotating gantry, with the radiation source configured to project a beam of radiation through an object and towards the multislice detector array. The multislice detector array is configured to sense attenuation of the radiation passing through the object. The imaging system is configured to helically scan an object with a computed tomographic imaging system to acquire a plurality of views of projection data at a plurality of gantry angles and a plurality of cone angles, generate a plurality of cone angle dependent weights that are inversely correlated to an absolute value of a cone angle, and weight the projection data using the cone angle dependent weights.

In still another aspect, a computer for collecting computed tomography (CT) scan data is provided. The computer is programmed to helically scan an object with a computed tomographic imaging system to acquire a plurality of views of projection data at a plurality of gantry angles and a plurality of cone angles, generate a plurality of cone angle dependent weights that are inversely correlated to an absolute value of a cone angle, and weight the projection data using the cone angle dependent weights.

DETAILED DESCRIPTION OF THE INVENTION

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a single slice fan beam helical scan. The helix mapped out by the fan beam yields projection data from which images in each prescribed slice may be reconstructed.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
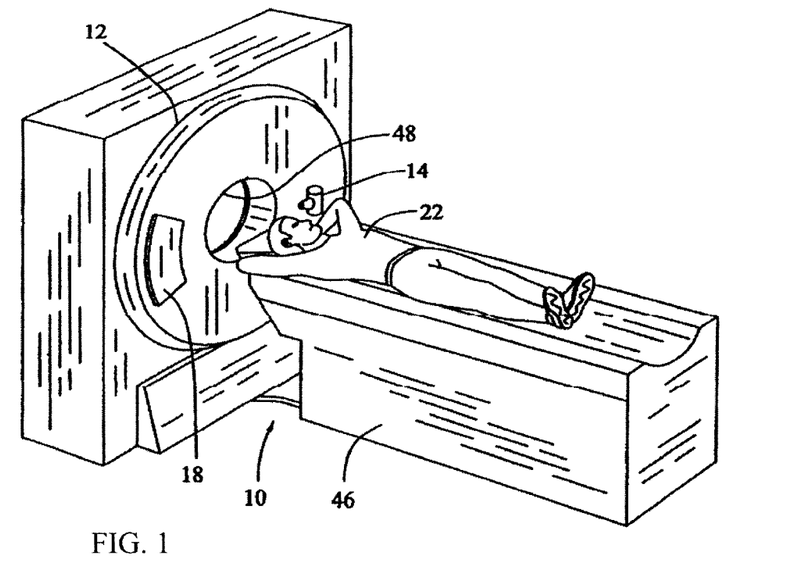
FIG. 1 is a pictorial view of a CT imaging system embodiment.
Figure 2:
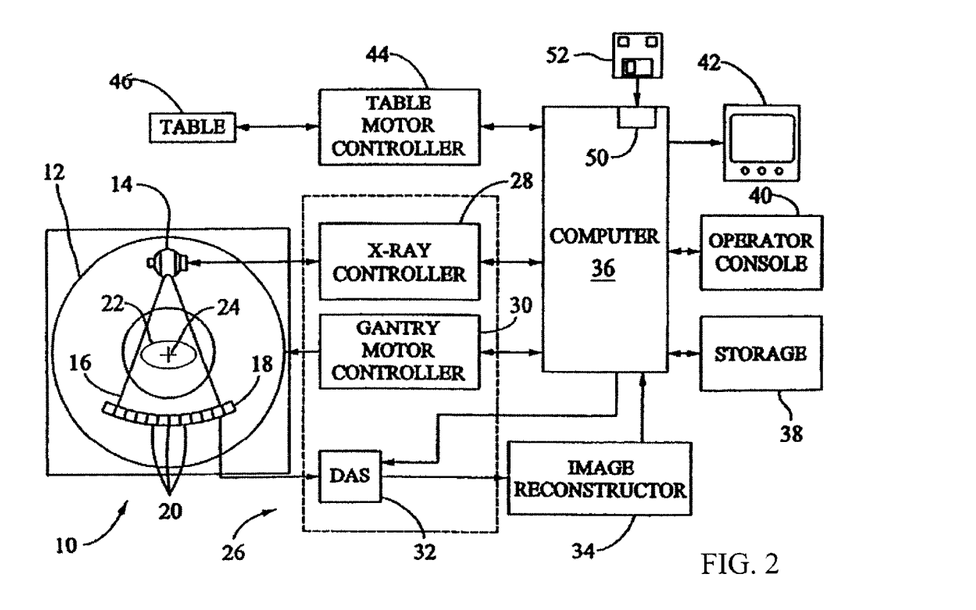
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) each row including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 3:
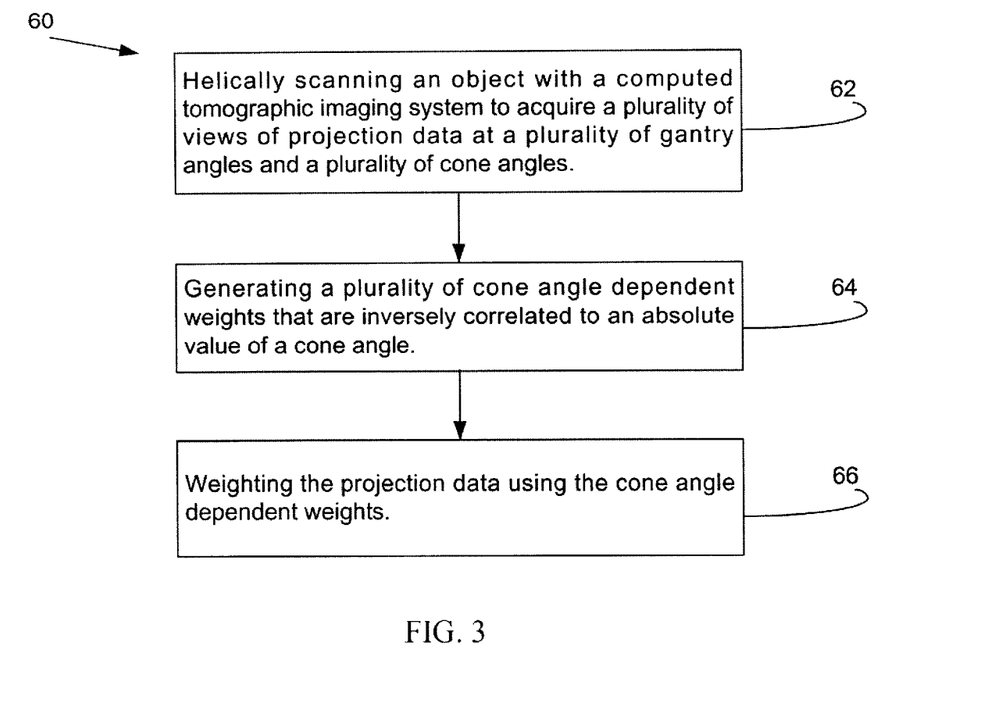
FIG. 3 illustrates a method for reconstructing an image of an object.

FIG. 3 illustrates a method 60 for reconstructing an image of an object. In an exemplary embodiment, method 60 for weighting of projection data includes helically scanning 62 an object with a computed tomographic imaging system to acquire a plurality of views of projection data at a plurality of gantry angles and a plurality of cone angles, generating 64 a plurality of cone angle dependent weights that are inversely correlated to an absolute value of a cone angle, and weighting 66 the projection data using the cone angle dependent weights.

Figure 4:
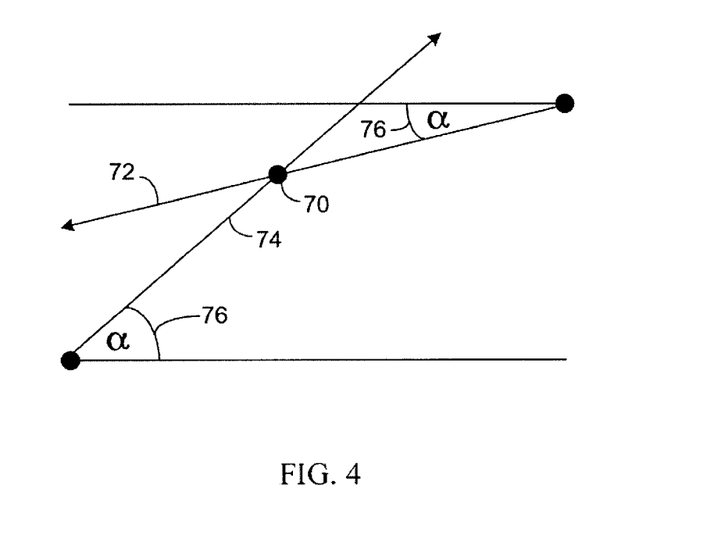
FIG. 4 illustrates the varying cone angles of rays passing through a voxel.

FIG. 4 illustrates varying cone angles of rays passing through a reconstruction voxel 70. Reconstruction voxel 70 is sampled by a plurality of conjugate rays 72, 74 having different cone angles 76, at least one of which contributes to a reconstruction value at voxel 70. Ray 72 has a smaller cone angle α than ray 74 and is therefore more consistent than ray 74. One embodiment of the cone angle dependent weighting described herein assigns greater weight to more consistent data than to less consistent data. Low pitch scans collect data only when a focal spot is near enough to a plane of reconstruction (POR) so that all rays are measured. As helical pitch increases, focal spot positions furthest from the POR do not measure all rays for voxels near the edge of the field of view, with the result that for high pitch scans certain data is extrapolated and combined with measured data to generate reconstructions. High pitch scans are defined as those scans in which normalized helical pitch p is defined as p>1.

Figure 5:
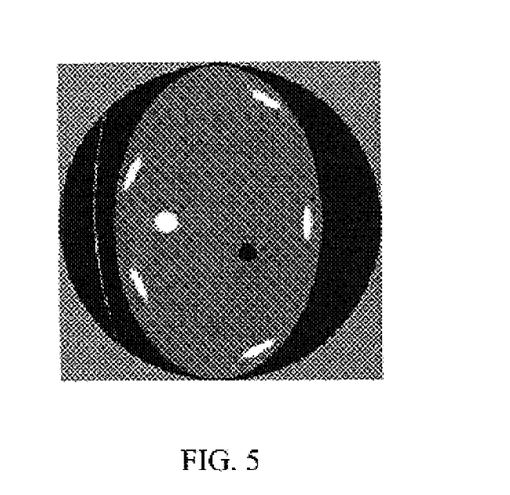
FIG. 5 is a reconstruction of data helically scanned at 9/8 normalized pitch using standard half scan weights.

The Feldkamp reconstruction of volumetric CT data is a perturbation of a standard two-dimensional filtered-backprojection (FBP) of classical axial CT scans. Axial CT scans with full gantry rotation collect mathematically redundant data. A family of partial scan weights was developed to reduce scan time by reducing the number of views required for reconstruction. For fan-beam geometries with CT system-defined fan angle Γ, scan time can be reduced by a factor of $$\frac{\pi/2 + \Gamma}{\pi}$$

by any consistent weighting function $\omega(\beta,\gamma)$ satisfying:

$\omega(\beta,\gamma) + \omega(\beta_c,\gamma_c) = 1$ $\omega(\beta,\gamma) = 1 \; \forall |\beta| < (\pi/2 - \Gamma)$ where $(\beta,\gamma)$ and $(\beta_c,\gamma_c)$ parameterize a plurality of conjugate rays 72, 74. Application of this weighting scheme, which was derived for 2D axial scanning and is independent of cone angle, to helical multi-slice data is shown in FIG. 5. Shown is a reconstruction of 8 row×2.5 mm data collected at 9/8 normalized pitch using standard half scan weights. In one complete gantry rotation the focal spot translated 9*2.5 mm=22.5 mm along the z-axis, requiring relatively little data extrapolation for this low-pitch scan.

Figure 6:
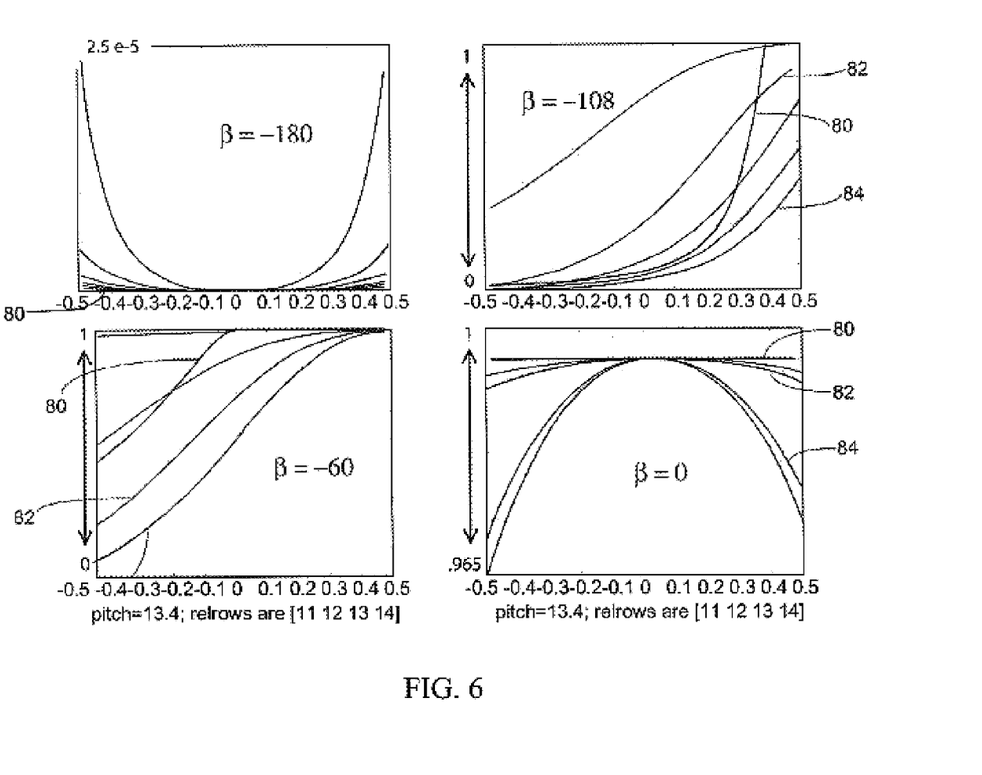
FIG. 6 illustrates weights vs. $\gamma$ for various gantry positions $\beta$.

In use, partial scan weightings are described which are used to generate data as shown in FIGS. 5 and 6. A range of views such as is used for reconstruction is symmetric about an origin, $\beta\in[-\pi/2+\Gamma_\omega), (\pi/2+\Gamma_\omega))$, where $\Gamma_\omega$ is a user-defined fan angle such that $\Gamma_\omega \geq \Gamma$. Conjugate rays are related to one another according to the following relationship:

$$\beta_c=\beta+\pi-2\gamma; \text{ and}$$

$$\gamma_c=-\gamma.$$

The source-voxel distance in the POR, L, is defined as:

$$FS(\beta) = (R\cos\beta, R\sin\beta, t\beta)$$

$$v = (x, y, z)$$

$$L = \sqrt{(R\cos\beta - x)^2 + (R\sin\beta - y)^2}$$

where:

FS($\beta$) is a focal spot location for a gantry angle $\beta$;
R is a radius of gantry rotation;
$\beta$ is a gantry angle;

$$t = pN \times (\text{slice width}) \times \frac{\beta}{2\pi}$$

p is a normalized pitch;
N is a number of slices;
v is a voxel; and
(x,y,z) are coordinates of the voxel.

The source-voxel distance for the conjugate of L is $L_c=2R\cos\gamma-L$ and $\tan\alpha=(z-t\beta)/L$. For a user-defined fan angle $\Gamma_\omega$ the weights are identically zero when $|\beta|>(\pi/2+\Gamma_\omega)$ and inversely proportional to cone angle $\alpha$. One embodiment of the weighting function is thus defined as:

$$w_q(\alpha, \beta, \gamma) = \frac{2g^q}{(g^q + g_c^q)}$$

where:
$g=\max(0,((\pi/2+\Gamma_\omega)-|\beta|))|\tan\alpha_c|$;
$g_c=\max(0,((\pi/2+\Gamma_\omega)-|\beta_c|))|\tan\alpha|$;
q>1;
$\alpha$ is a cone beam angle;
$\beta$ is a gantry angle;
$\gamma$ is a fan beam angle;
$\alpha_c$ is a cone beam angle of a conjugate ray;
$\beta_c=\beta+\pi-2\gamma$;
$\gamma_c=-\gamma$;
$\Gamma$ is a hardware-defined cone angle for the CT system;
$\Gamma_\omega$ is a used-defined fan angle for a fan-beam geometry; and
$\Gamma_\omega \geq \Gamma$.

In use, completely consistent rays, that is, those rays having a cone beam angle a equal to zero, lying in a POR are given full weight:

$$\omega_q(0,\beta,\gamma)=2 \;\forall\gamma, |\beta|<(\pi/2-\Gamma_\omega).$$

Figure 7:
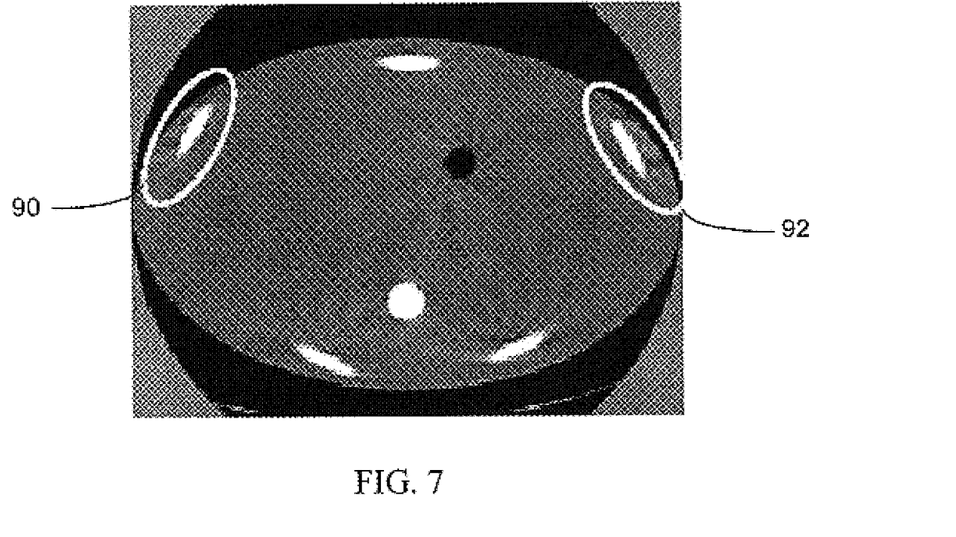
FIG. 7 is a reconstruction of data helically scanned at a normalized pitch of 13.4/8 using standard half scan weights.
Figure 8:
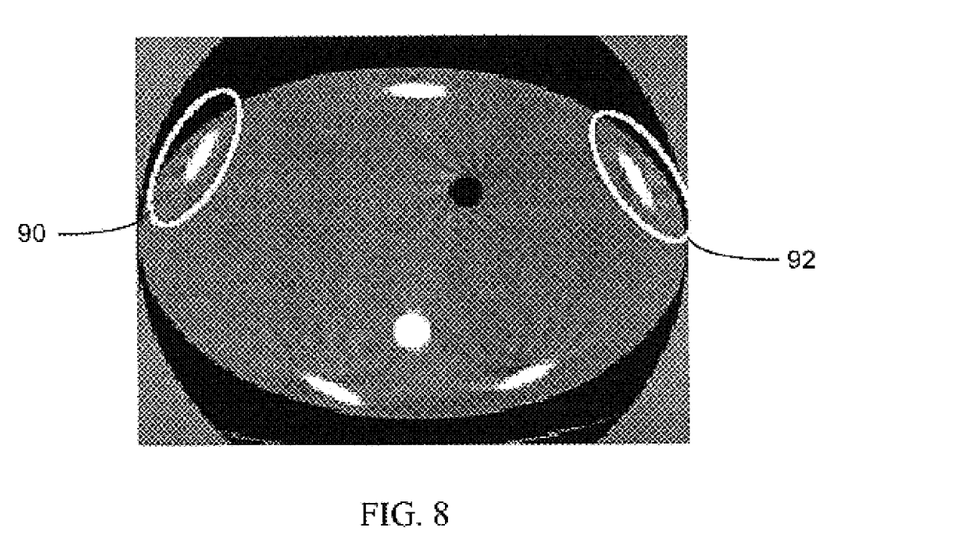
FIG. 8 is a reconstruction of data helically scanned at a normalized pitch of 13.4/8 using cone angle dependent weights.

FIGS. 6, 7, and 8 show results generated from data collected with a full gantry rotation and user-defined fan angle $\Gamma_\omega=\pi/2$. FIG. 6 shows plots of weighting function $\omega_q$ vs. fan angle $\gamma$ for a plurality of gantry angles $\beta$ assuming 8 rows×2.5 mm data collected at 13.4/8 normalized pitch. Each of the four panels in FIG. 6 shows weighting function $\omega_q$ vs. fan angle $\gamma$ for a different value of gantry angle $\beta$, as indicated inside each panel. Shown are cone angle minimizing weights for each row contributing to reconstruction of a 40 cm field of view. Solid, bold lines 80 correspond to standard half scan weights, which do not depend on cone angle. Solid, thin lines 82 correspond to measured data, while dashed lines 84 correspond to extrapolated data. In FIG. 6 more views are used in reconstruction than are used for the reconstructions presented in FIG. 7. However, the first and last views are given little weight, with $\omega_q$<2.5 e-5, that these views do not substantially contribute to the reconstruction, as shown in the upper left panel of FIG. 5. As gantry angle $\beta$ approaches zero, weighting function $\omega_q$ tends to weight measured rows more heavily than extrapolated rows.

FIG. 7 shows a reconstruction performed on 8 row×2.5 mm data collected at 13.4/8 normalized pitch using standard half scan weighting. FIG. 8 shows a reconstruction performed on 8 row×2.5 mm data collected at 13.4/8 normalized pitch using cone angle dependent weighting. As shown in FIG. 8, the reconstruction generated with a cone angle dependent weighting scheme as described herein has improved image quality, particularly near structure 90 and structure 92, as compared to structure 90 and structure 92 generated using half scan weighting and shown in FIG. 7.

In an alternative embodiment, weighting function $\omega(\alpha,\beta,\gamma)$ is based on Parker's partial scan weights:

$$w(\alpha, \beta, \gamma) = \frac{[P(\beta, \gamma)^p(\cot\alpha)^{2a}]}{[P(\beta, \gamma)^p(\cot\alpha)^{2a} + P(\beta_c, \gamma_c)^p(\cot\alpha_c)^{2a}]}$$

where:
$\alpha \geq 0$;
p=helical pitch, normalized to a number of detector rows;
$P(\beta,\gamma)^p$ is a function for Parker's partial scan weights;
$\alpha$ is a cone beam angle;
$\beta$ is a gantry angle;
$\gamma$ is a fan angle;
$\alpha_c$ is a cone beam angle of a conjugate ray;
$\beta_c=\beta+\pi-2\gamma$; and
$\gamma_c=-\gamma$.

In use, $\omega(\alpha,\beta,\gamma)=1$ when $P(\beta,\gamma)^p=1$ and $\omega(\alpha,\beta,\gamma)=0$ when $P(\beta,\gamma)^p=0$. Also, when a=0 and p=1 then $\omega(\alpha,\beta,\gamma)=P(\beta,\gamma)^p$. For axial scans p=0 and therefore $\omega(\alpha,\beta,\gamma)$ is a function of cone angle $\alpha$ and is independent of Parker partial scan weights $P(\beta,\gamma)$. When reconstructing a central plane, $\alpha=\alpha_c=0$ and thus $\omega(\alpha,\beta,\gamma)=\frac{1}{2}$. To produce partial scan weights for axial scans p is increased from zero to a positive value when computing $\omega(\alpha,\beta,\gamma)$. The weighting function $\omega(\alpha,\beta,\gamma)$ is a smooth, consistent weighting function satisfying:

$$\omega(\alpha,\beta,\gamma)+\omega(\alpha_c,\beta_c,\gamma_c)\equiv 1.$$

While the invention has been described in terms of various specific embodiments, those skilled in the art will recognize that the invention can be practiced with modification within the spirit and scope of the claims.

What is claimed is:

1. A method for reconstructing an image of an object utilizing a computed tomographic (CT) imaging system having a radiation source and a multislice detector array on a rotating gantry, the radiation source configured to project a beam of radiation through an object and towards the multislice detector array, the multislice detector array configured to sense attenuation of the radiation passing through the object, said method comprising:

scanning an object with a computed tomographic imaging system to acquire a plurality of views of projection data at a plurality of gantry angles and a plurality of cone angles;

generating a plurality of cone angle dependent weights that are a function of a conjugate ray; and weighting the projection data using the cone angle dependent weights.

2. A method in accordance with claim 1 wherein said weighting the projection data comprises weighting measured data and extrapolated data.

3. A method in accordance with claim 2 further comprising weighting the measured data more heavily than the extrapolated data.

4. A method in accordance with claim 1 wherein said scanning an object with a computed tomographic imaging system to acquire a plurality of views of projection data at a plurality of gantry angles and a plurality of cone angles further comprises helically scanning an object with a normalized pitch p such that:

$$p \geq N$$

where:

N is a number of detector rows.

5. A method in accordance with claim 1 wherein said generating a plurality of cone angle dependent weights comprises generating a plurality of cone angle dependent weights in accordance with:

$$w_q(\alpha, \beta, \gamma) = \frac{2g^q}{(g^q + g_c^q)}$$

where:

$g = \max(0, ((\pi/2 + \Gamma_\omega) - |\beta|)) |\tan \alpha_c|$;
$g_c = \max(0, ((\pi/2 + \Gamma_\omega) - |\beta_c|)) |\tan \alpha|$;
$q \geq 1$;
$\alpha$ is a cone beam angle;
$\beta$ is a gantry angle;
$\gamma$ is a fan beam angle;
$\alpha_c$ is a cone beam angle of a conjugate ray;
$\beta_c = \beta + \pi - 2\gamma$;
$\gamma_c = -\gamma$;
$\Gamma$ is a hardware-defined cone angle for the CT system;
$\Gamma_\omega$ is a user-defined fan angle for a fan-beam geometry; and
$\Gamma_\omega \geq \Gamma$.

6. A method in accordance with claim 1 wherein said scanning an object with a computed tomographic imaging system to acquire a plurality of views of projection data at a plurality of gantry angles and a plurality of cone angles further comprises helically scanning an object with a normalized pitch p such that:

$$0 \leq p \leq N$$

where:

N is a number of detector rows.

7. A computed tomographic (CT) imaging system for reconstructing an image of an object, said computed tomographic (CT) imaging system comprises a radiation source and a multislice detector array on a rotating gantry, said radiation source configured to project a beam of radiation through an object and towards said multislice detector array, said multislice detector array configured to sense attenuation of said radiation passing through the object;

said imaging system configured to:

scan an object with a computed tomographic imaging system to acquire a plurality of views of projection data at a plurality of gantry angles and a plurality of cone angles;

generate a plurality of cone angle dependent weights that are a function of a conjugate ray; and weight the projection data using the cone angle dependent weights.

8. An imaging system in accordance with claim 7 wherein said scanning an object with a computed tomographic imaging system to acquire a plurality of views of projection data at a plurality of gantry angles and a plurality of cone angles further comprises helically scanning an object with a normalized pitch p such that:

$$0 \leq p \leq N$$

where:

N is a number of detector rows.

9. An imaging system in accordance with claim 7 wherein said scanning an object with a computed tomographic imaging system to acquire a plurality of views of projection data at a plurality of gantry angles and a plurality of cone angles further comprises helically scanning an object with a normalized pitch p such that:

$$p \geq N$$

where:

N is a number of detector rows.

10. An imaging system in accordance with claim 7 wherein said generating a plurality of cone angle dependent weights comprises generating a plurality of cone angle dependent weights in accordance with:

$$w_q(\alpha, \beta, \gamma) = \frac{2g^q}{(g^q + g_c^q)}$$

where:

$g = \max(0, ((\pi/2 + \Gamma_\omega) - |\beta|)) |\tan \alpha_c|$;
$g_c = \max(0, ((\pi/2 + \Gamma_\omega) - |\beta_c|)) |\tan \alpha|$;
$q \geq 1$;
$\alpha$ is a cone beam angle;
$\beta$ is a gantry angle;
$\gamma$ is a fan beam angle;
$\alpha_c$ is a cone beam angle of a conjugate ray;
$\beta_c = \beta + \pi - 2\gamma$;
$\gamma_c = -\gamma$;
$\Gamma$ is a hardware-defined cone angle for the CT system;
$\Gamma_\omega$ is a user-defined fan angle for a fan-beam geometry; and
$\Gamma_\omega \geq \Gamma$.

11. An imaging system in accordance with claim 7 wherein said weighting the projection data comprises weighting measured data and extrapolated data.

12. An imaging system in accordance with claim 11 further comprising weighting the measured data more heavily than the extrapolated data.

13. A computer for collecting computed tomography (CT) scan data, said computer programmed to:

scan an object with a computed tomographic imaging system to acquire a plurality of views of projection data at a plurality of gantry angles and a plurality of cone angles;

generate a plurality of cone angle dependent weights that are a function of a conjugate ray; and weight the projection data using the cone angle dependent weights.

14. A computer in accordance with claim 13 wherein to scan an object with a computed tomographic imaging system to acquire a plurality of views of projection data at a plurality of gantry angles and a plurality of cone angles said computer configured to helically scan an object with a normalized pitch p such that:

$$p \geq 1$$

where:

N is a number of detector rows.

15. A computer in accordance with claim 13 wherein to generate a plurality of cone angle dependent weights said computer configured to generate a plurality of cone angle dependent weights in accordance with:

$$w_q(\alpha, \beta, \gamma) = \frac{2g^q}{(g^q + g_c^q)}$$

where:

g=max(0,((π/2+Γ_ω)−|β|))|tan α_c|;

g_c=max(0,((π/2+Γ_ω)−|β_c|))|tan α|;

q≥1;

α is a cone beam angle;

β is a gantry angle;

γ is a fan beam angle;

α_c is a cone beam angle of a conjugate ray;

β_c=β+π−2γ;

γ_c=−γ;

Γ is a hardware-defined cone angle for the CT system;

Γ_ω is a user-defined fan angle for a fan-beam geometry; and

Γ_ω≥Γ.

16. A computer in accordance with claim 13 wherein to generate a plurality of cone angle dependent weights said computer configured to generate a plurality of cone angle dependent weights in accordance with:

$$w(\alpha, \beta, \gamma) = \frac{[P(\beta, \gamma)^p (\cot \alpha)^{2a}]}{[P(\beta, \gamma)^p (\cot \alpha)^{2a} + P(\beta_c, \gamma_c)^p (\cot \alpha_c)^{2a}]}$$

where:

α≧0;

p=helical pitch, normalized to a number of detector rows;

P(β,γ)^p is a function for Parker's partial scan weights;

α is a cone beam angle;

β is a gantry angle;

γ is a fan angle;

α_c is a cone beam angle of a conjugate ray;

β_c=+π−2γ; and

γ_c=−γ.

17. A computer in accordance with claim 13 wherein to weight the projection data said computer programmed to weight measured data and extrapolated data.

18. A computer in accordance with claim 17 wherein to weight measured data and extrapolated data said computer programmed to weight the measured data more heavily than the extrapolated data.

19. A computer in accordance with claim 13 wherein to scan an object with a computed tomographic imaging system to acquire a plurality of views of projection data at a plurality of gantry angles and a plurality of cone angles said computer configured to helically scan an object with a normalized pitch p such that:

$$0 \leq p \leq N$$

where:

N is a number of detector rows.

* * * * *

UNITED STATES PATENT AND TRADEMARK OFFICE
CERTIFICATE OF CORRECTION

PATENT NO. : 6,754,299 B2　　　　　　　　　　　　　　　　　　　　　Page 1 of 1
DATED : June 22, 2004
INVENTOR(S) : Sarah K. Patch It is certified that error appears in the above-identified patent and that said Letters Patent is hereby corrected as shown below:

Column 9,
Line 12, delete "$p \geq 1$" and insert therefor -- $p \geq N$ --.

Signed and Sealed this

Thirtieth Day of August, 2005

JON W. DUDAS
*Director of the United States Patent and Trademark Office*